United States Patent
Baïkoff et al.

(10) Patent No.: US 6,712,847 B2
(45) Date of Patent: Mar. 30, 2004

(54) SCLERAL EXPANSION SEGMENT (75) Inventors: Georges Baïkoff, Marseille (FR); Scott Hampton, Cumming, GA (US)

(73) Assignee: O.I.I. International, Inc., Ontario, CA (US)

( * ) Notice: Subject to any disclaimer, the term of this patent is extended or adjusted under 35 U.S.C. 154(b) by 0 days.

(21) Appl. No.: 09/833,958

(22) Filed: Apr. 12, 2001

(65) Prior Publication Data

US 2002/0161433 A1 Oct. 31, 2002

Related U.S. Application Data (63) Continuation of application No. PCT/FR99/02487, filed on Oct. 13, 1999.

(30) Foreign Application Priority Data

Oct. 13, 1998 (FR) .............................................. 98 12834

(51) Int. Cl.$^7$ .................................................. A61F 2/14
(52) U.S. Cl. ........................................ 623/4.1; 623/5.11
(58) Field of Search .................................. 623/4.1, 6.41, 623/6.42, 6.43, 5.11, 5.12, 5.13

(56) References Cited

U.S. PATENT DOCUMENTS

| 5,370,607 | A  |   | 12/1994 | Memmen |        |
|-----------|----|---|---------|--------|--------|
| 5,489,299 | A  | * | 2/1996  | Schachar | 623/4.1 |
| 5,628,795 | A  | * | 5/1997  | Langerman | 623/4.1 |
| 6,007,578 | A  |   | 12/1999 | Schachar |      |
| 6,206,919 | B1 | * | 3/2001  | Lee    | 623/5.12 |
| ,002,403  | A1 |   | 1/2002  | Zdenek et al. |  |

FOREIGN PATENT DOCUMENTS

| WO | WO 9515719  | 2/1995 |
| WO | WO 95/03755 | 6/1995 |

* cited by examiner

Primary Examiner—David H. Willse
Assistant Examiner—Hieu Phan (57) ABSTRACT

The disclosure concerns a scleral expansion segment of the type consisting of an arched rod designed to be placed on the sclera perpendicular to the ciliary body. The free ends of said rod have a spatula shape wider than the diameter of said bridge, so as to constitute wide support bases.

6 Claims, 5 Drawing Sheets

FIG. 11

SCLERAL EXPANSION SEGMENT

CROSS REFERENCE TO RELATED APPLICATIONS

This application is a continuation of international application Serial No. PCT/FR99/02487 filed Oct. 13, 1999, which claims priority as a continuation-in-part of French patent application Serial No. 98/12834 filed Oct. 13, 1998, which issued as French Patent No. 98/12834 as of Dec. 8, 2000.

BACKGROUND OF THE INVENTION

The present invention concerns, in general, the correction of vision by insertion of a corrective element in the eye and, more specifically, the correction of presbyopia.

According to new theories, presbyopia is not linked solely to the loss of flexibility of the crystalline lens on aging, but is mainly due to increase of the diameter of said crystalline lens with age.

Figure 8:
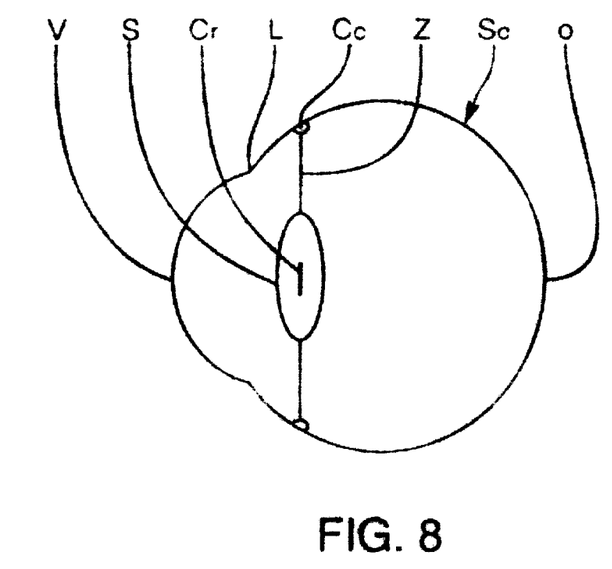
FIG. 8 is a schematic section of an eye.

As schematically represented in FIG. 8, the crystalline lens Cr contained in the crystalline lens sac S is suspended from the sclera Sc along a ring of the latter located behind the limbus L separating the vitreous body V from the opaque body O. This ring is, on the average, situated at a latitude spaced from 2 to 3 mm apart from the limbus, if the optical axis is taken as reference. Said suspension of the crystalline lens is secured by a ligament Z called zonule attached to the ciliary body Cc. As the size of the scleral ring and ciliary body Cc do not vary in time, the zonule Z is gradually expanded in the course of enlargement of the crystalline lens Cr and partially loses its traction power on the equator of the crystalline lens sac S.

A new surgical method has therefore been proposed to correct presbyopia, consisting of increasing the diameter of the scleral ring in the ciliary body, so as to stretch the zonule, which will again be able to perform its function of deformation of the crystalline lens under the effect of contraction of the ciliary muscle and return the power of accommodation to the eye.

For the use of this method of treatment, Schachar proposed a truncated cone-shaped ring set in place by suture around the scleral ring (U.S. Pat. No. 5,465,737).

However, this ring requires a very long and difficult surgical intervention and entails unpleasant sequelae for the patients.

Arched segments have therefore been recently proposed, which are set in place in loops incised in the thickness of the sclera concentric to the limbus, perpendicular to the ciliary body, and which constitute stiffeners exerting an outward traction stretching the zonule. In practice, four scleral segments are placed at 90°.

Figure 9:
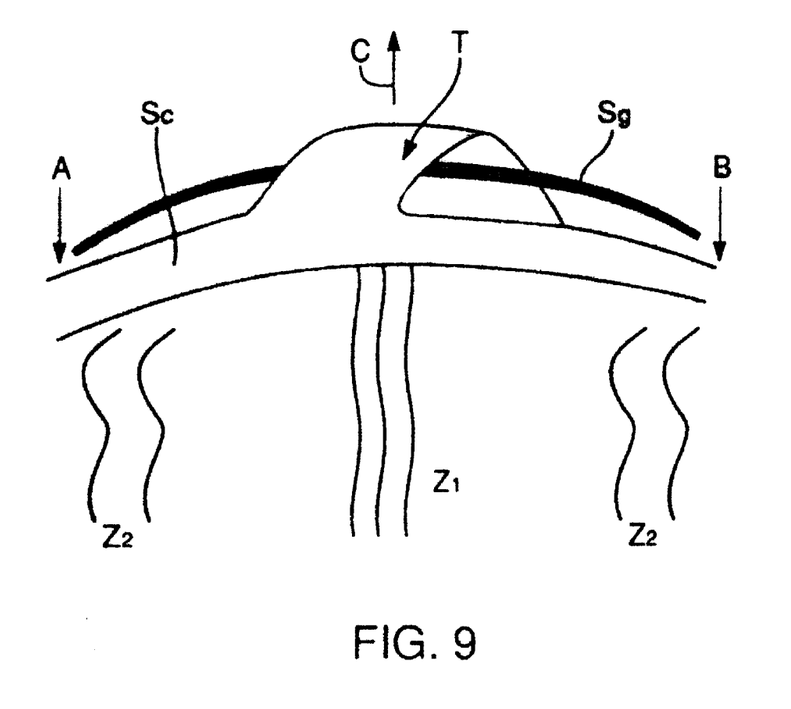
FIG. 9 is a partial schematic section of an eye equipped with a scleral expansion segment.

This intervention is much more effective than placement of the complete ring initially proposed by Schachar, for the surgical procedure is simple and rapid (incision of four tunnels constituting the loops and insertion of the segments) and eliminates any suture, therefore considerably diminishing the patient's discomfort and operating sequelae. This technique is schematically illustrated in FIG. 9.

This figure shows a sclera fragment Sc, in which a tunnel T has been formed, like a belt loop.

The segment Sg has been inserted in this loop and rests at its bases A and B on the sclera, on which it bears, while its bridge C exerts an outward traction force. It can be seen that the zonule is expanded $Z_1$ perpendicular to force C and relaxed $Z_2$ perpendicular to forces A and B.

However, the present segments, which are simple cylindrical rods, present a sizable risk of perforation of the sclera by reason of the fact that they punctually bear on the latter.

The purpose of this invention is to eliminate this disadvantage and to propose scleral expansion segments which present no risk of perforation of the sclera.

SUMMARY OF THE INVENTION

According to the invention, the scleral expansion segment which, in a manner known per se, consists of an arched rod designed to be placed on the sclera perpendicular to the ciliary body, is characterized in that its free ends have a spatula shape wider than the diameter of said rod, so as to constitute wide support bases.

The segment according to the invention is further remarkable in that:

the bases have a radius of curvature R1 corresponding to that of the sclera perpendicular to the ciliary body, while the bridge has radius of curvature R2 less than R1;

it presents a multitude of perforations;

it is coated with a biocompatible synthetic material with porous surface;

it consists of a core of deformable material with shape memory, sunk in a layer of soft material;

it has an internal canal designed for placement of a core, the nature and strength of which can be chosen in order to adjust the effect of the scleral expansion segment;

the core consists of an injectable product;

it is made in two parts interlocking with each other;

the segment consists, on one side, of a bridge, one end of which is integral with a base, and, on the other, of a removable base, and in that complementary means of attachment are placed between the free end of the bridge and the removable base; and the two parts contain means for preventing any rotation in relation to each other.

BRIEF DESCRIPTION OF THE DRAWINGS

The invention will be better understood thanks to the specification which follows, given by way of nonlimitative example with reference to the attached drawings in which:

In FIGS. 10 to 15, the pieces functionally identical receive the same references as in FIGS. 1 to 9.

DETAILED DESCRIPTION OF THE INVENTION

Figure 1:
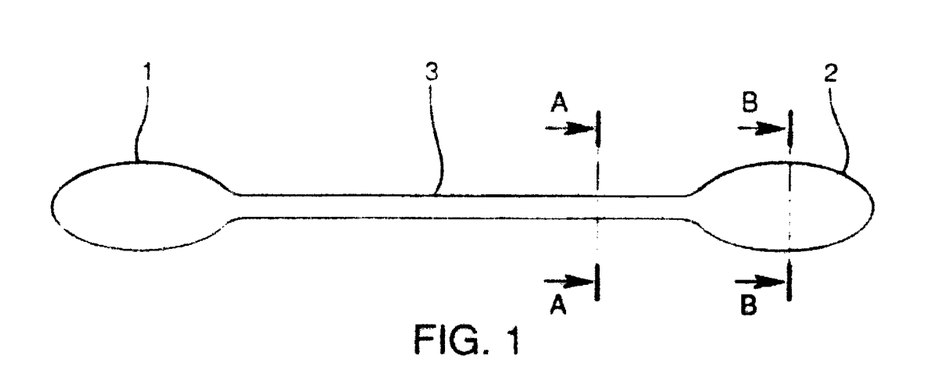
FIG. 1 is a schematic top view of a scleral expansion segment according to a first embodiment of the invention.

As represented in FIG. 1, the scleral expansion segment according to the invention consists of an arched rod having two ends forming two bases 1 and 2 connected by a cylindrical bridge 3. The bases 1 and 2 consist of parts wider than the diameter of the bridge 3, spatula-shaped, and their inner face is flattened. This arrangement makes possible the bearing of the scleral expansion segment on the sclera to be made on a relatively extended surface, which enables the pressure directed toward the inside of the eye, exerted on the surface of said sclera, to be reduced considerably.

Figure 2:
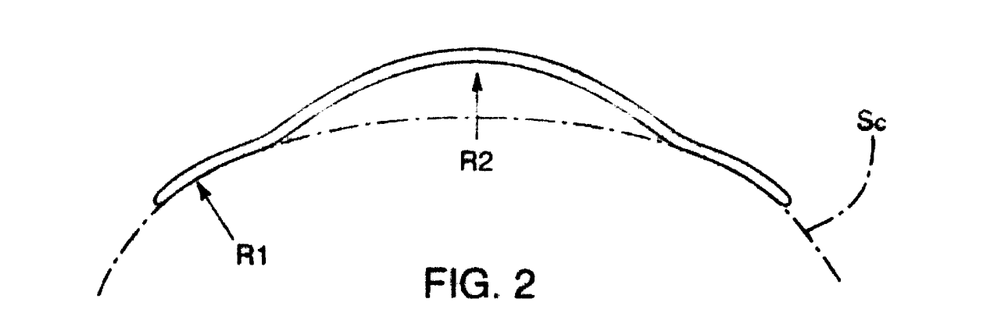
FIG. 2 is a side view of the scleral expansion segment of FIG. 1.

As is evident in FIG. 2, the scleral expansion segment, seen in longitudinal section, is an arched piece having two radii of curvature. The bases 1 and 2 have a radius of curvature R1 corresponding to that of the sclera Sc perpendicular to the ciliary body, while the bridge 3 has a radius of curvature R2 less than R1, so as to stretch over the scleral loop.

In the embodiments represented in FIGS. 1 to 6, said bases, seen from the top, have a an overall ellipsoidal shape. Their ends are rounded in order to avoid damaging the sclera.

The material used for manufacture of the scleral expansion segment is a biocompatible synthetic material, such as PMMA, polyhema or ceramic.

Figure 3:
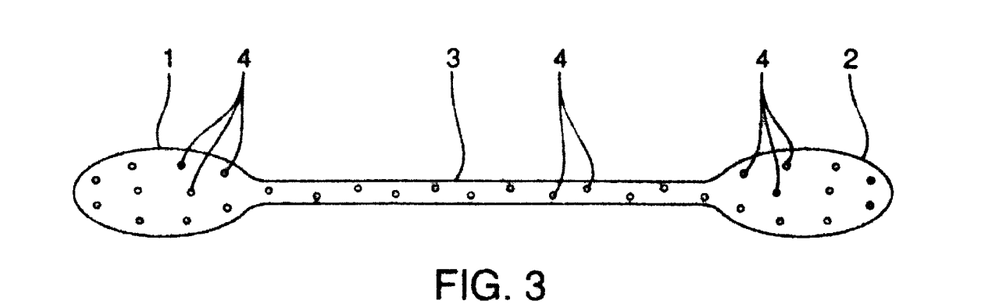
FIG. 3 is a top view of a scleral expansion segment according to a second embodiment of the invention.

In the working variant represented in FIG. 3, the scleral expansion segment has a multitude of perforations 4 through which the connective tissue can grow in order to improve attachment of the sclera to said correction segment and/or to serve as a point of passage for a possible suture, if necessary.

According to a variant not represented in the drawing, the creation of holes 4 can be replaced by providing a porous surface on the scleral expansion segment with openings wide enough to accept colonization by the connective tissue. Such a surface will, for example, be made by coating the segment with a bio-compatible synthetic material, a hydroxyapatite, a variable hydration component, etc.

The scleral expansion segment according to the invention can also be so conceived that its action is adjustable, that is, so that its shape can be modified to adjust its effect on the zonule upon placement or if it should diminish in time.

Figure 4A:
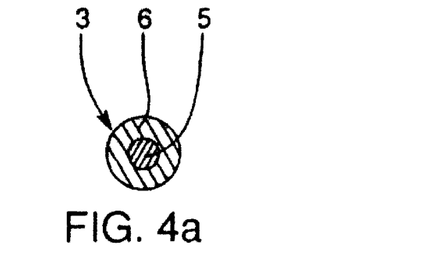
FIGS. 4a and 4b are sections respectively along lines A—A and B—B of FIG. 1.
Figure 4B:
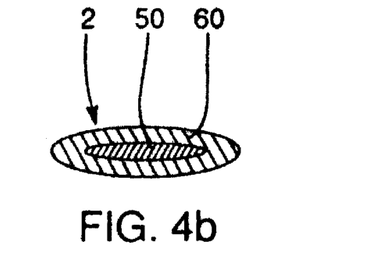

For that purpose, and as represented in FIGS. 4a and 4b, which respectively illustrate a section of the bridge 3 and a section of a base 1 or 2, the scleral expansion segment contains a core 5, 50 of rigid material capable of retaining the shape imparted to it, sunk in a soft material 6, 60.

The material constituting the core 5 is preferably chosen among deformable materials with shape memory.

According to an embodiment not represented in the drawing, the scleral expansion segment has an internal canal intended for placement of a core, the nature and strength of which can be chosen by the practitioner in order to adapt the effect of the scleral expansion segment to the state of the eye under care.

As the bridge 3 of the scleral expansion segment can have a diameter in the order of 0.6 millimeter, the internal canal intended to contain the core can have a diameter in the order of 0.2 millimeter.

Such a removable core can be made in the form of a solid body that is inserted in the scleral expansion segment.

It can also consist of an injectable product that is introduced in the canal formed in the scleral expansion segment, the effect of the scleral expansion segment then being adjusted by modulating the pressure of the product introduced in said segment.

The product injected in the canal of the scleral expansion segment can be a gas, or even a liquid or gel, polymerizable or not.

Owing to the fact that the scleral expansion segment according to the invention contains bases larger in size that the bridge cooperating with the loop incised in the sclera in which it is placed, it is to be understood that the surgeon will either have to make a wider incision or force a base of the segment into the loop. In the first case, he runs the risk of improper holding of the segment and insufficient traction of the segment on the zonule. In the second case, he risks damaging the sclera.

This is why, according to a particularly advantageous variant, the invention provides for making the scleral expansion segment in at least two interlocking parts and arranged so that at least one end of the bridge is free for insertion of the segment in the loop.

Figure 5:
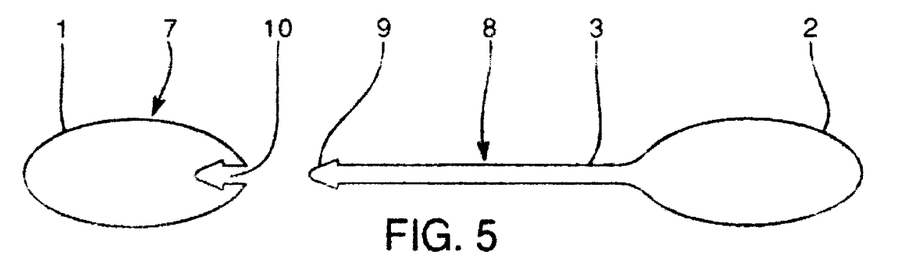
FIG. 5 is a top view of a scleral expansion segment according to a third embodiment of the invention.
Figure 6:
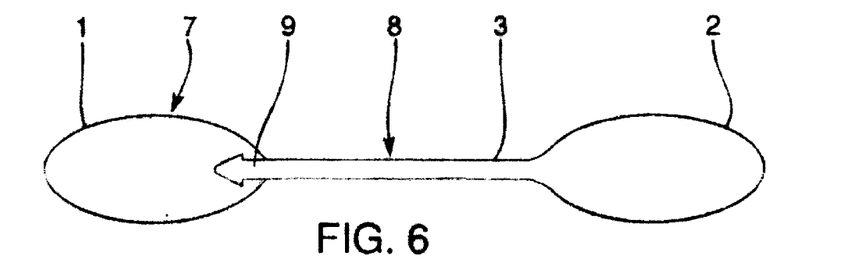
FIG. 6 shows the scleral expansion segment of FIG. 5 assembled.
Figure 7A:
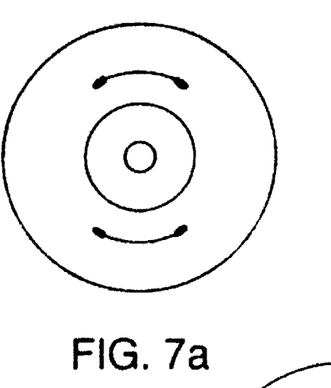
FIGS. 7a to 7c schematically represent examples of arrangements in the eye of the scleral expansion segments according to the invention.
Figure 7B:
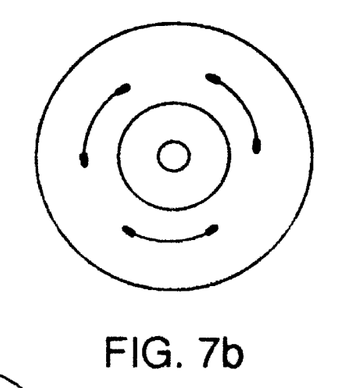
Figure 7C:
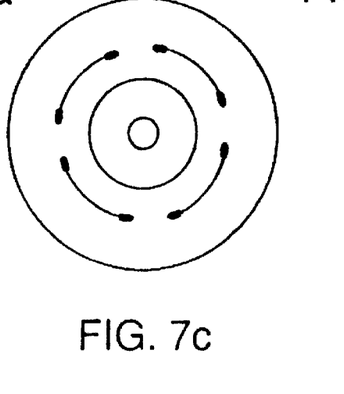

Such a segment is represented in FIGS. 5 and 6.

It consists of two parts 7 and 8, which can be attached to each other by means of attachment 9 and 10.

As can be seen in FIG. 5, the first part 7 contains a base, base 1 in the working example represented in the drawing, while the second part 8 contains the second base 2 and the bridge 3.

The end of the bridge 3 is shaped to constitute a means of attachment 9 fitted to cooperate with a complementary means of attachment 10 carried by the first part 7.

In the working example represented in the drawing, the bridge 3 of part 8 carries a generally harpoon-shaped male attachment 9 and part 7 has a female attachment 10 consisting of a cavity complementing the shape of the harpoon 9.

Preferably, in order to avoid any risk of trauma, rounded end shapes will be used for attachment means 9 and 10.

Also preferably, in order to avoid any error in connection between the two pieces or untimely rotation of one piece in relation to the other after connection, grooves will be made on the periphery of the free end of the bridge (for example, 3 grooves over 120°), cooperating with corresponding grooves on the inner periphery of the cavity 10 engaging the base of the segment.

It was indicated at the beginning of this specification that the segments are generally arranged in 4's roughly at 90°, perpendicular to the ciliary body at approximately 3 mm behind the limbus (FIG. 6c), but other arrangements can be adopted, for example, two segments in polar positions (FIG. 6a) or three segments at 120° (FIG. 6b).

By way of indication, the scleral expansion segments have a length in the order of 3 to 5 millimeters, their base having, for example, a width ranging between 1 and 2 millimeters.

FIGS. 10 to 15 represent different advantageous embodiments of the scleral expansion segment according to the invention.

It was indicated above that the function of the bases 1 and 2 was to distribute the bearing forces of the segment on the sclera over a wide surface, with the result of reducing the pressure directed toward the eye.

In practice, the inventor observed that the bridge was exerting an outward traction force on the sclera, while the bases react by exerting an opposite pressure.

It is the outward traction force exerted that stretches the zonule and consequently restores the optical properties of the crystalline lens.

In order to prevent that traction effect from being diminished or destroyed by the pressure of the bases on the sclera, it is advantageous to eliminate any risk of bearing of the bases in the plane of the zonule Z.

For that purpose, the invention provides for the bases of the segment to be so shaped that their area of contact with the sclera lies outside the plane of the zonule. More precisely, the area of contact of the bases will have to be separated at least 1 mm on both sides of the median longitudinal axis of the bridge of the scleral expansion segment.

Several arrangements can be used to achieve that condition. For example, the part of the bases situated on the median longitudinal axis can be given a concavity directed downward, or the bases can be arranged on both sides of the bridge, or else a combination of those two solutions can be adopted.

Figure 10:
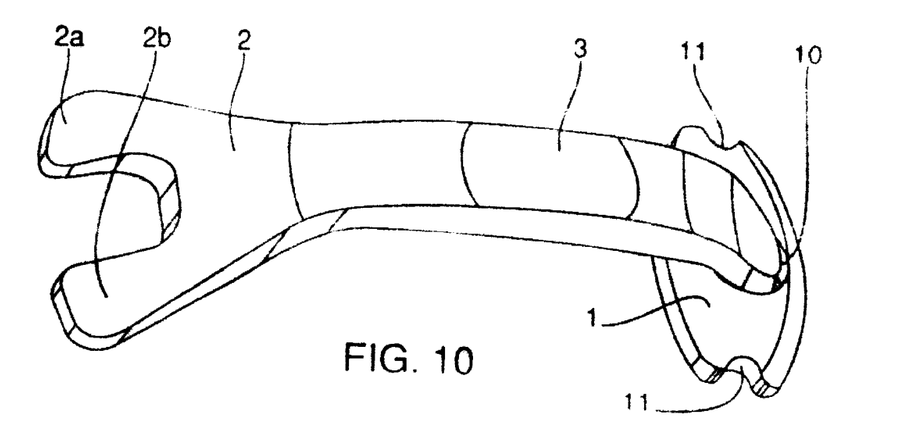
FIG. 10 is a schematic view in top perspective of a third embodiment of a scleral expansion segment according to the invention.
Figure 11:
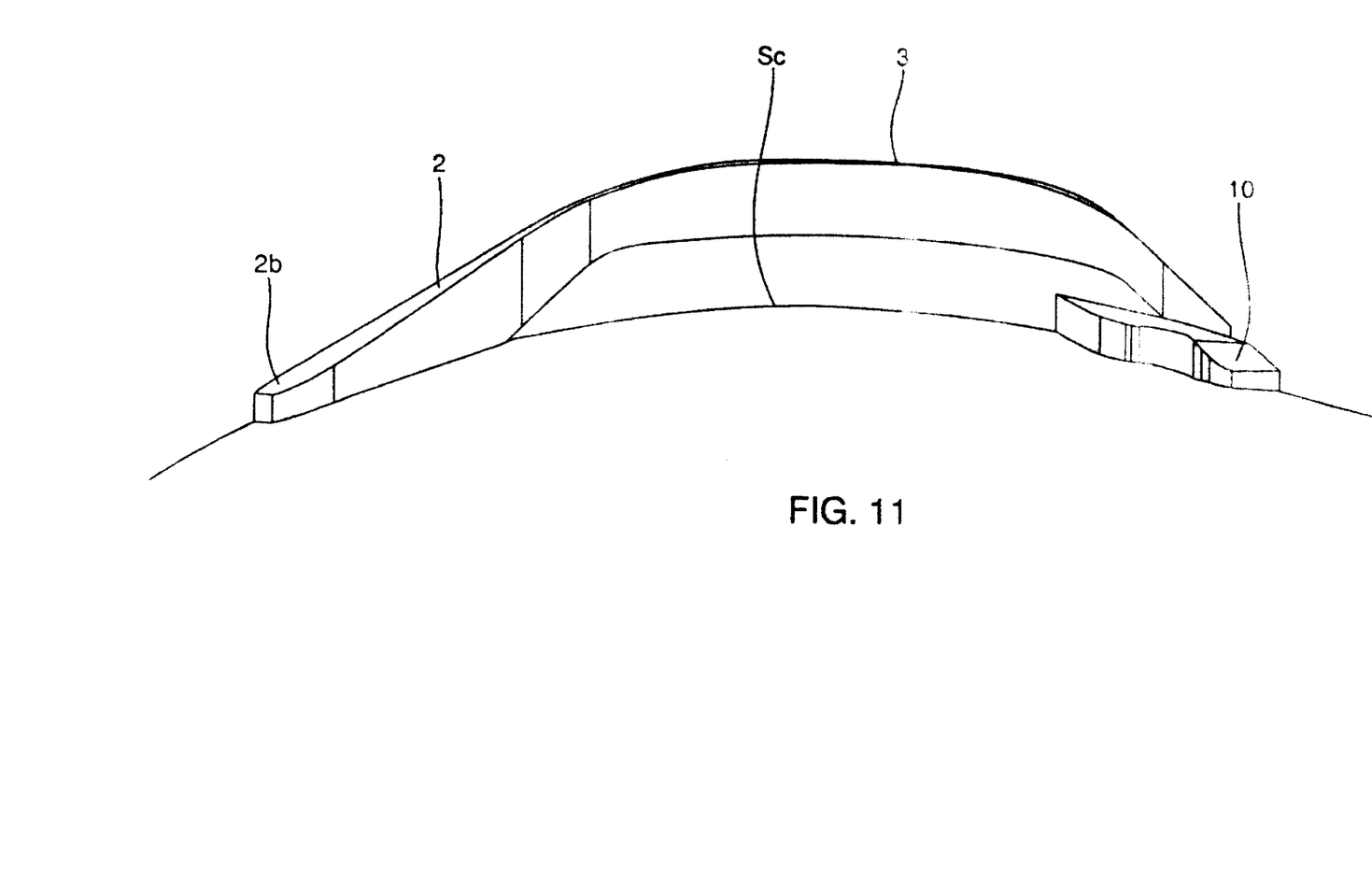
FIG. 11 is a profile of the embodiment of FIG. 10.

In the example of FIGS. 10 and 11, the segment consists of two parts, that is, one single-piece main part containing a bridge 3 combined with a base 1, whose bearing parts 2a and 2b are separated like a fork, and a complementary part consisting of a removable support 1 which contains on its upper face a recess 10 in which the free end of the bridge 3 is engaged.

In FIG. 10 it can be seen that the removable support 1 has a generally oval shape with recesses 11 at its top, forming a gripping point for the tools used on placement of the segment.

Thus, on placement of the segment, it is sufficient to lift the free end of the bridge 3, for example, with a surgical forceps of the Bonn forceps type, to engage the base or removable support 1 below and to arrange it with its hole in alignment with the free end of the bridge, and then relax the latter in order to ensure an attachment of the bridge 3 on the base 2. The hole may possibly be filled with biocompatible glue to obtain a permanent attachment.

The terminal part of the bridge 3 cooperating with the hole 10 of the removable support 1 may present under its lower face a stud, lug or base (not represented) of shape concordant with that of the hole 10.

The construction could also be reversed, with a removable base bearing a stud, lug or boss projecting on its upper face cooperating with a hole or recess machined under the end of the bridge.

In the same manner as provided with the recesses 11 to facilitate gripping of the removable base 1, similar means can also be arranged, such as grooves or ribs (not represented) on the side edges of the free end of the bridge 3.

In addition, in order to prevent any sliding of the bases bearing on the sclera, the lower face of the bases can also present a rough surface, burrs, ridges, etc.

FIGS. 12 to 15 present very schematically still other embodiments of a scleral expansion segment according to the invention.

Figure 12:
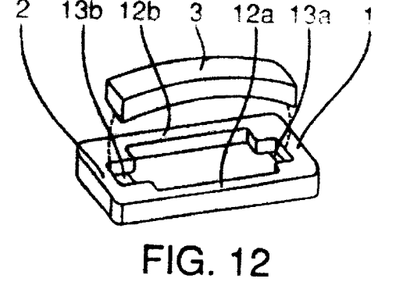
FIGS. 12, 13, 14a, 14b and 15 are schematic illustrations of other embodiments of the invention.

In FIG. 12, the bases 1 and 2 are joined together by rods 12a and 12b so as to form a single-piece frame on which the free ends of the bridge 3 are locked in recesses 13a and 13b.

Figure 13:
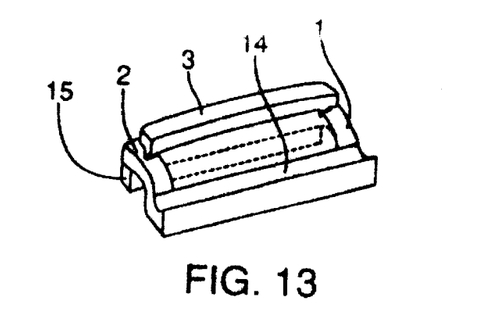

In FIG. 13, the scleral expansion segment is in three pieces, namely, a bridge 3, two arched bases 1 and 2 joined by a rod 14 parallel to the bridge 3 and a second removable rod 15 arranged parallel to the rod 14 opposite the bridge 3 and on which the free end of the bases 1 and 2 is attached.

Figure 14A:
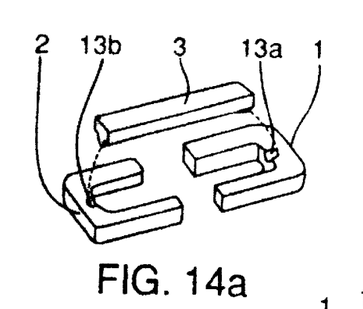

FIG. 14a represents a variant of FIG. 12, in which the bases 1 and 2 are not joined together to form a frame, but separated with their free ends opposite each other.

In said embodiment, the useful length of the bridge 3 can be very close to the overall length of the segment, which is advantageous in order to keep the length of the segment at a low value, preferably less than 8 mm, while obtaining an optimal length for the bridge.

Figure 14B:
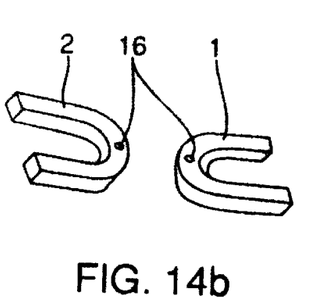

In FIG. 14b, bases 1 and 2 are alone presented with their free ends directed opposite each other and holes 16 receiving the free end of the bridge not represented.

Figure 15:
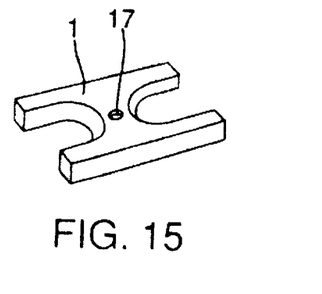

In FIG. 15, a generally H-shaped single removable base (1) is represented with the locking hole 17 of the end of the bridge, situated on the crossbar of the H.

In addition to the safety and facility of placement they provide, the scleral expansion segments according to the invention have the advantage of being very easy to deposit and modify in the course of the operation in order to adapt the curvature of their bridge to the outward traction desired.

Working examples have been described above, in which the scleral expansion segment has a cylindrical rod-shaped bridge, but, without departing from the scope of the invention, the bridge could have any other shape (sheet, band, etc.), once that bridge is connected to extended bases and/or those bases present bearing areas arranged outside the plane of the zonule. The bridge can advantageously be given a section with transverse concavity directed downward. This arrangement makes it possible to place the traction forces on the sclera with better precision in relation to the zonule.

Without departing from the scope of the invention, means can also be provided to adjust the height of the bridge in relation to the bases, such as screws, cams, wedges or other devices inserted between the ends of the bridge and the bases.

Finally, if a surgical procedure should be necessary on the eye bearing segments according to the invention, said segment can easily be removed either by disengaging them or by sectioning them in proximity to one of the support bases.

We claim:

1. A vision corrective element for implantation in the sclera perpendicular to the ciliary body, the vision corrective element comprising an arched segment having a length, a width, a thickness, a central bridge portion, a first end portion and an opposed second end portion, each of the end portions having a width greater than their thicknesses and greater than the width of the bridge portion.

2. The vision corrective element of claim 1 wherein the first end portion is integral with the bridge and the second end portion is removable from the bridge.

3. The vision corrective element of claim 2 wherein the first end portion is fork-shaped.

4. The vision corrective element of claim 2 wherein the second end portion comprises a face recess in which the bridge is engaged.

5. The vision corrective element of claim 4 wherein the second end portion comprises an aperture sized and dimensioned to be engaged by a corresponding male portion on the bridge portion.

6. The vision corrective element of claim 2 wherein the second end portion has recesses on its upper face forming a gripping point for insertion tools.

* * * * *

(12) EX PARTE REEXAMINATION CERTIFICATE (6538th)
United States Patent
Baïkoff et al.

(10) Number: US 6,712,847 C1
(45) Certificate Issued: Nov. 25, 2008

(54) SCLERAL EXPANSION SEGMENT (75) Inventors: Georges Baïkoff, Marseille (FR); Scott Hampton, Cumming, GA (US)

(73) Assignee: Opthalmic Lenders, LLC, Dallas, TX (US)

Reexamination Request:
No. 90/007,026, May 4, 2004
No. 90/008,195, Aug. 25, 2006
No. 90/008,415, Jan. 12, 2007

Reexamination Certificate for:
Patent No.: 6,712,847
Issued: Mar. 30, 2004
Appl. No.: 09/833,958
Filed: Apr. 12, 2001

Related U.S. Application Data (63) Continuation of application No. PCT/FR99/02487, filed on Oct. 13, 1999.

(30) Foreign Application Priority Data

Oct. 13, 1998 (FR) .............................................. 98 12834

(51) Int. Cl.
*A61F 2/14* (2006.01)

(52) U.S. Cl. ........................................ 623/4.1; 623/5.11
(58) Field of Classification Search ........................ None
See application file for complete search history.

(56) References Cited

U.S. PATENT DOCUMENTS

| 5,323,788 | A | * | 6/1994 | Silvestrini et al. | 623/5.12 |
| 5,370,607 | A | * | 12/1994 | Memmen | 604/8 |
| 5,489,299 | A | * | 2/1996 | Schachar | 623/4.1 |
| 5,628,795 | A | * | 5/1997 | Langerman | 623/4.1 |
| 6,007,578 | A | * | 12/1999 | Schachar | 623/11.11 |
| 6,197,056 | B1 | | 3/2001 | Schachar | |
| 6,206,919 | B1 | * | 3/2001 | Lee | 623/5.12 |
| 6,280,468 | B1 | | 8/2001 | Schachar | |
| 6,428,572 | B2 | * | 8/2002 | Nagai | 623/4.1 |
| 6,712,847 | B2 | * | 3/2004 | Baikoff et al. | 623/4.1 |
| 2002/0002403 | A1 | * | 1/2002 | Zdenek et al. | 623/4.1 |
| 2002/0161433 | A1 | * | 10/2002 | Baikoff et al. | 623/4.1 |
| 2004/0034412 | A1 | * | 2/2004 | Schachar | 623/4.1 |

FOREIGN PATENT DOCUMENTS

| WO | WO9515719 | * | 2/1995 |
| WO | WO9503755 | * | 6/1995 |

* cited by examiner

*Primary Examiner*—Beverly M. Flanagan (57) ABSTRACT

The disclosure concerns a scleral expansion segment of the type consisting of an arched rod designed to be placed on the sclera perpendicular to the ciliary body. The free ends of said rod have a spatula shape wider than the diameter of said bridge, so as to constitute wide support bases.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 9–18:

As represented in FIG. 1, the scleral expansion segment according to the invention consists of an arched rod having two ends forming two bases 1 and 2 connected by a cylindrical bridge 3. *When viewed from the top, as illustrated in FIG. 1, the scleral expansion segment is essentially linear.* The bases 1 and 2 consist of parts wider than the diameter of the bridge 3, spatula-shaped, and their inner face is flattened. This arrangement makes possible the bearing of the scleral expansion segment on the sclera to be made on a relatively extended surface, which enables the pressure directed toward the inside of the eye, exerted on the surface of said sclera, to be reduced considerably.

AS A RESULT OF REEXAMINATION, IT HAS BEEN DETERMINED THAT:

Claims 1–6 are cancelled.

\* \* \* \* \*